(12) United States Patent
Gorny

(10) Patent No.: US 7,811,549 B2
(45) Date of Patent: Oct. 12, 2010

(54) METHODS, COMPOSITIONS, UNIT DOSAGE FORMS, AND KITS FOR PHARMACOLOGIC STRESS TESTING WITH REDUCED SIDE EFFECTS

(75) Inventor: Philippe Gorny, Paris (FR)

(73) Assignee: Adenobio N.V. (NL)

( * ) Notice: Subject to any disclaimer, the term of this patent is extended or adjusted under 35 U.S.C. 154(b) by 412 days.

(21) Appl. No.: 11/772,684

(22) Filed: Jul. 2, 2007

(65) Prior Publication Data

US 2008/0064654 A1 Mar. 13, 2008

Related U.S. Application Data

(60) Provisional application No. 60/818,928, filed on Jul. 5, 2006.

(51) Int. Cl.
*A61K 31/7076* (2006.01)
*A61P 9/08* (2006.01)
(52) U.S. Cl. .............. 424/9.3; 424/9.1; 424/9.4
(58) Field of Classification Search ........ None
See application file for complete search history.

(56) References Cited

U.S. PATENT DOCUMENTS

| | | | |
|---|---|---|---|
| 4,751,224 A | 6/1988 | Argwal et al. | |
| 4,912,092 A | 3/1990 | Gruber | |
| 5,070,877 A | 12/1991 | Mohiuddin et al. | |
| 5,075,290 A | 12/1991 | Findley et al. | |
| 5,231,086 A | 7/1993 | Sollevi | |
| 5,524,622 A | 6/1996 | Wilson | |
| 5,552,267 A | 9/1996 | Stern et al. | |
| 5,622,867 A | 4/1997 | Livesey et al. | |
| 5,629,298 A | 5/1997 | Dobson, Jr. | |
| 5,731,296 A | 3/1998 | Sollevi | |
| 5,780,450 A | 7/1998 | Shade | |
| 5,811,547 A | 9/1998 | Nakamichi et al. | |
| 5,877,180 A | 3/1999 | Linden et al. | |
| 5,919,614 A * | 7/1999 | Livesey et al. ............. 435/2 |
| 5,932,558 A | 8/1999 | Cronstein et al. | |
| 5,942,497 A | 8/1999 | Fukunaga et al. | |
| 5,998,386 A | 12/1999 | Feldman | |
| 6,020,321 A | 2/2000 | Cronstein et al. | |
| 6,221,669 B1 | 4/2001 | Livesey et al. | |
| 6,221,851 B1 | 4/2001 | Feldman | |
| 6,288,113 B1 | 9/2001 | Egi et al. | |
| 6,322,771 B1 | 11/2001 | Linden et al. | |
| 6,331,543 B1 | 12/2001 | Garvey et al. | |
| 6,447,443 B1 | 9/2002 | Keogh et al. | |
| 6,448,235 B1 | 9/2002 | Linden et al. | |
| 6,449,507 B1 | 9/2002 | Hill et al. | |
| 6,462,044 B2 | 10/2002 | Garvey et al. | |
| 6,531,457 B2 | 3/2003 | Linden et al. | |
| 6,532,388 B1 | 3/2003 | Hill et al. | |
| 6,628,987 B1 | 9/2003 | Hill et al. | |
| 6,690,973 B2 | 2/2004 | Hill et al. | |
| 6,718,208 B2 | 4/2004 | Hill et al. | |
| 6,735,471 B2 | 5/2004 | Hill et al. | |
| 6,904,306 B1 | 6/2005 | Wu et al. | |
| 6,924,114 B2 | 8/2005 | Wyant et al. | |
| 6,955,814 B1 | 10/2005 | Dobson | |
| 7,011,938 B2 | 3/2006 | Macey | |
| 7,184,828 B2 | 2/2007 | Hill et al. | |
| 7,184,829 B2 | 2/2007 | Hill et al. | |
| 2002/0044968 A1 | 4/2002 | Van Lengerich | |
| 2002/0138109 A1 | 9/2002 | Keogh et al. | |
| 2003/0035843 A1 | 2/2003 | Livesey et al. | |
| 2003/0077229 A1 | 4/2003 | Dugger, III | |
| 2003/0220280 A1 | 11/2003 | Bunge et al. | |
| 2004/0053392 A1 | 3/2004 | Williams | |
| 2004/0162584 A1 | 8/2004 | Hill et al. | |
| 2004/0267110 A1 | 12/2004 | Tremble | |
| 2005/0025713 A1 | 2/2005 | Dugger, III | |
| 2005/0058688 A1 | 3/2005 | Boerger et al. | |
| 2005/0065324 A1 | 3/2005 | Williams | |
| 2005/0080260 A1 | 4/2005 | Mills et al. | |
| 2005/0165030 A1 | 7/2005 | Liu et al. | |

(Continued)

FOREIGN PATENT DOCUMENTS

EP     0984280 A1     3/2000

(Continued)

OTHER PUBLICATIONS

Kim, Young-Hoon and Kim, Chan-Hyung and Kim, Myung-Suk, Korean J Physiol Pharmacol, Differential Modulation of Exogenous and Endogenous Adenosine-induced Coronary Vasodilation by Dipyridamole, (2001), vol. 5, pp. 423-431.*

(Continued)

*Primary Examiner*—Shaojia Anna Jiang
*Assistant Examiner*—Bahar Schmidtmann
(74) *Attorney, Agent, or Firm*—Dechert LLP

(57) ABSTRACT

Methods are presented that comprise the administration of a pharmaceutical composition comprising adenosine and dipyridamole, as well methods comprising the combined administration of dipyridamole administered as a bolus with adenosine given as an infusion, both at dosages below their respective single agent dosages, for detecting the presence and/or assessing the severity of myocardial ischemia during pharmacologic stress tests. The methods are useful for exploiting the vasodilating abilities of adenosine at doses at which side effects related to adenosine are substantially reduced while optimal coronary artery perfusion is achieved. Also presented are compositions, unit dosage forms, and kits that are useful in performing the methods.

41 Claims, No Drawings

U.S. PATENT DOCUMENTS

| | | |
|---|---|---|
| 2005/0214877 A1 | 9/2005 | Wyant et al. |
| 2006/0018933 A1 | 1/2006 | Vaya et al. |
| 2006/0018934 A1 | 1/2006 | Vaya et al. |
| 2006/0024365 A1 | 2/2006 | Vaya et al. |
| 2006/0025756 A1 | 2/2006 | Francischelli et al. |
| 2006/0057033 A1 | 3/2006 | Goldenberg |
| 2006/0166901 A1 | 7/2006 | Yu et al. |
| 2006/0173301 A1 | 8/2006 | Darlas |
| 2006/0210478 A1 | 9/2006 | Weisskoff |
| 2006/0211045 A1 | 9/2006 | George et al. |
| 2006/0240014 A1 | 10/2006 | Sukhatme |
| 2006/0257474 A1 | 11/2006 | Nakagawa et al. |
| 2006/0257947 A1 | 11/2006 | Williams |
| 2007/0031340 A1 | 2/2007 | Hale et al. |
| 2007/0116729 A1 | 5/2007 | Palepu |
| 2007/0141096 A1 | 6/2007 | Van Lengerich |
| 2007/0141182 A1 | 6/2007 | Niazi |
| 2007/0161543 A1 | 7/2007 | Yu et al. |
| 2007/0207222 A1 | 9/2007 | Yu et al. |
| 2007/0213308 A1 | 9/2007 | Lessem et al. |
| 2007/0224240 A1 | 9/2007 | Toner et al. |
| 2007/0249558 A1 | 10/2007 | Picano |
| 2008/0003213 A1 | 1/2008 | Lessem |
| 2008/0003214 A1 | 1/2008 | Cezanne et al. |
| 2008/0009498 A1 | 1/2008 | Garvey et al. |

FOREIGN PATENT DOCUMENTS

| | | |
|---|---|---|
| WO | WO 00/78774 A2 | 12/2000 |
| WO | WO 02/39124 A1 | 5/2002 |

OTHER PUBLICATIONS

Sollevi et al., 1984, "Controlled Hypotension with Adenosine in Cerebral Aneurysm Surgery," *Anesthesiology*, 61:400-405.

Conradson, et al., 1987, "Cardiovascular Effects of Infused Adenosine in Man: Potentiation by Dipyridamole," *Acta Physiologica Scandinavica*, 129(3):387-391.

Mahmarian, et al., May 1994, "Myocardial Perfusion Imaging During Pharmacologic Stress Testing," *Cardiology Clinics*, 12(2):223-245.

Nott, 1970, "The Possible Role of Adenosine in the Coronary Dilator Action of Some Pyrimidopyrimidines and Pteridines," *Br. J. Pharmac.*, 39(2):287-295.

PCT International Search Report from PCT/EP2007/005923 dated Oct. 17, 2007.

"Summary of the Product Characteristics," http://www.adenosin.com/en/en_SPC_05.pdf.

* cited by examiner

METHODS, COMPOSITIONS, UNIT DOSAGE FORMS, AND KITS FOR PHARMACOLOGIC STRESS TESTING WITH REDUCED SIDE EFFECTS

1. CROSS REFERENCE TO RELATED APPLICATIONS

This application claims benefit under 35 U.S.C. §119(e) to provisional application Ser. No. 60/818,928, filed Jul. 5, 2006, the disclosure of which is incorporated herein by reference in its entirety.

2. BACKGROUND

Functional assessment of myocardium, in particular the evaluation of the myocardium's oxygen status, is important in guiding therapeutic decisions in the care of patients with cardiac ischemia. In current clinical practice, myocardial ischemia status is most often assessed using non-invasive nuclear perfusion imaging methodologies, such as planar scintigraphy or single photon emission computed tomography (SPECT), with thallium and technetium as the most frequently used isotopes. More recently, positron emission tomography (PET) with rubidium-82 has been gaining recognition as providing improved images with less radiation. Semi-invasive transesophageal doppler echography is also useful to study the motion of ventricular walls, and non-invasive transthoracic doppler echocardiography is an easy and non-invasive methodology for measurement of coronary flow reserve.

These functional tests typically require that the patient's heart be "stressed", either through controlled exercise or by pharmacologic means, and are thus generically and colloquially known as "stress tests". Pharmacological stressors for functional assessment of myocardium act through coronary vasodilation: by dilating normal vessels to a greater extent than diseased vessels, these agents establish a shunt, or "myocardial steal", that produces differential increases in blood flow in healthy vs. diseased arteries in patients with coronary artery disease, optimizing the discriminatory imaging of cardiac muscle areas in need of oxygen supply.

Adenosine and dipyridamole are coronary vasodilators, each of which is approved for individual use as a pharmacologic stressor for stress testing. Adenosine acts directly by stimulating adenosine purinergic P1 receptors on the arterial wall. Dipyridamole is believed to work indirectly by blocking reuptake of adenosine at the cellular level, leading to an increase in endogenous adenosine concentration in the blood. Dipyridamole produces similar near-maximal coronary hyperemia to that produced by exogenous adenosine, but less quickly.

To ensure near-maximal coronary vasodilation, and to provide sufficient time for the acquisition of cardiac images, adenosine is infused for 6 minutes at a dosage rate of 140 µg/kg patient body weight/min; dipyridamole is infused for 4 minutes at 140 µg/kg patient body weight/min. Thus, the total recommended dose of adenosine is 0.84 mg/kg, and the total recommended dose for dipyridamole is 0.56 mg/kg at the minimum and 0.80 mg/kg on average in a 4 minute infusion. If vasodilation is insufficient, the total dose of dipyridamole can be increased up to 0.95 mg/kg, administered over a 6 minute infusion.

Although infused for only a few minutes, compounds that stimulate adenosine receptors are accompanied by numerous uncomfortable adverse effects. With adenosine, the most frequently reported are flushing (44%), chest pain or chest discomfort (40%), dyspnea (28%), headache (18%), throat or neck or jaw discomfort (15%), and gastrointestinal discomfort (13%); other side effects are less frequent.

The adverse effects of adenosine are dose-dependent. Symptoms such as heat sensation, flushed face, dyspnea and chest pain increase as adenosine dosage is increased from 60 to 140 µg/kg/min, in a six minute infusion. Chest pain typically appears at doses of 90 µg/kg/min, and becomes frequent at 120 µg/kg/min. At a dosage of 70 µg/kg/min or less, it has been noted that adenosine adverse reactions are very few and of mild intensity. However, when administered by intravenous perfusion at 70 µg/kg/min or less, or even at 90-120 µg/kg/min, adenosine shows reduced efficacy, and is not recommended for stress testing at such reduced dosages.

The side effect profile of dipyridamole is similar, but with adverse events occurring less often. However, dipyridamole side effects last longer, are more difficult to manage, and thus more frequently require the administration of intravenous aminophylline as an antidote.

Because dipyridamole is understood to act by increasing endogenous adenosine, use of both adenosine and dipyridamole at full intravenous dosage is contraindicated. Analogously, oral intake of dipyridamole prior to an adenosine pharmacologic stress testing is generally avoided.

In an effort to reduce side effects at maximally effective agonist doses, adenosinergic agents are being developed that are selective for the A2a receptor subtype. See, e.g., U.S. Pat. Nos. 6,531,457; 6,448,235; 6,322,771; and 5,877,180. Specific compounds in development include regadenoson, binodenoson and apadenoson (BMS068645). However, despite their receptor selectivity, only modest reductions in side effects have been observed with these compounds. In addition, the compounds have a longer duration of action than adenosine; accordingly, the side effects, e.g., flushing, headache, and dyspnea, are longer lasting. Thus, although more specific than adenosine, these agents may be more likely to trigger prolonged side effects, and to require administration of pharmacologic antidotes, than is adenosine itself, whose side effects rapidly dissipate once administration is stopped. Moreover, none of these selective agents has yet been approved for clinical use.

There thus exists a continuing need in the art for injectable agents that can be used for pharmacologic stress testing that have the rapid onset and short half-life of adenosine, and thus can be managed clinically in the same manner as adenosine, and that provide maximal efficacy with reduced side effects.

3. SUMMARY

Although dipyridamole is believed to act indirectly by increasing adenosine concentration, and in clinical practice has a side effect profile similar to that of adenosine, I have now discovered that extremely low parenteral doses of dipyridamole—on the order of 5% of the dose now used clinically in cardiac imaging studies—can potentiate the vasodilation effects of adjunctively administered adenosine without commensurate potentiation of adenosine's side effects. This permits adenosine to be used at reduced dosage to effect coronary vasodilation, e.g., for functional assessment of myocardial function, with equal or superior efficacy as compared to current protocols, yet with reduced side effects. Moreover, the clinical and hemodynamic effects advantageously stop less than one minute after cessation of adenosine administration.

Accordingly, described herein are methods, compositions, unit dosage forms and kits that exploit this newly discovered phenomenon.

In a first aspect, methods of effecting coronary vasodilation for cardiac diagnosis are provided. The method comprises concurrently administering adenosine and dipyridamole, wherein adenosine and dipyridamole are administered parenterally at an adenosine:dipyridamole weight ratio of about 2:1 to about 10:1.

In certain embodiments of the method, the adenosine:dipyridamole ratio is about 2:1 to 4:1, such as 4:1; in various other embodiments, the adenosine:dipyridamole ratio is about 7:1 or about 8:1.

In various embodiments of the method, adenosine is administered at a dosage rate of 35 to 100 µg/kg/min and dipyridamole is administered at a dosage rate of 3.5-50 µg/kg/min. In some embodiments, adenosine is administered at a dosage rate of 70 µg/kg/min and dipyridamole is administered at a dosage rate of 10 µg/kg/min; adenosine is administered at a dosage rate of 70 µg/kg/min and dipyridamole is administered at a dosage rate of 8.75 µg/kg/min; adenosine is administered at a dosage rate of 50 µg/kg/min and dipyridamole is administered at a dosage rate of 12.5-25 µg/kg/min.

Adenosine and dipyridamole may be parenterally administered continuously for a period of at least about 2 minutes, typically less than about 6 minutes. In certain embodiments, adenosine and dipyridamole are parenterally administered continuously for a period of about 4 minutes.

In some embodiments of the methods presented herein, adenosine and dipyridamole are administered as a single composition. In other embodiments, adenosine and dipyridamole are administered from separate compositions.

In a variety of embodiments, at least one adenosine and dipyridamole is administered by intravenous infusion. In some embodiments, at least one adenosine and dipyridamole is administered by intra-atrial or intra-arterial administration. In some embodiments, the dosage of that agent can be adjusted downward using a dosage multiplier of 1/200-1/400, as compared to the intravenous dosage. In embodiments in which adenosine and/or dipyridamole is administered by intra-coronary administration, the dosage of that agent can be adjusted downward using a dosage multiplier of 1/200-1/400, as compared to the intravenous dosage.

In certain embodiments, the method usefully further comprises the step of assessing cardiac function. Assessing cardiac function may include use of one or more techniques selected from the group consisting of: electrocardiography, M mode echography, two dimensional echography, three dimensional echography, echo-doppler, cardiac imaging, planar (conventional) scintigraphy, single photon emission computed tomography (SPECT), dynamic single photon emission computed tomography, positron emission tomography (PET), first pass radionuclide angiography, equilibrium radionuclide angiography, nuclear magnetic resonance (NMR) imaging, perfusion contrast echocardiography, digital subtraction angiography (DSA), and ultrafast x-ray computed tomography (CINE CT). In certain embodiments, functional assessment is performed by SPECT; in other embodiments, the assessment is performed by PET.

In certain embodiments of the methods that further comprise assessment of cardiac function, assessing cardiac function includes parenteral administration of an isotope. The isotope is typically administered no less than 2.5 minutes after the concurrent parenteral administration of adenosine and dipyridamole has begun. In some embodiments isotope can be administered no less than 2.55 minutes, no less than 2.6 minutes, no less than 2.65 minutes, no less than 2.7 minutes, no less than 2.75 minutes after the concurrent administration of adenosine and dipyridamole has begun. In some embodiments isotope can be administered about 2.5-2.75 minutes after the concurrent parenteral administration of adenosine and dipyridamole has begun.

In a second aspect, methods are provided for effecting coronary vasodilation for cardiac diagnosis. These methods comprising: (i) parenterally administering dipyridamole; and (ii) concurrently or sequentially thereafter parenterally administering an adenosine receptor agonist. Each of dipyridamole and the adenosine receptor agonist is administered at a dosage lower than that required for maximal coronary vasodilation when administered as a single agent by identical parenteral route.

In some embodiments, the adenosine receptor agonist is selected from the group consisting of: adenosine, adenosine triphosphate (ATP), adenosine diphosphate (ADP), adenosine monophosphate (AMP), and pro-drugs and pharmaceutically acceptable salts of adenosine or AMP, ADP, ATP.

Each route of parenteral administration may be independently selected from the group consisting of: intra-arterial, intravenous, and atrial administration. In some embodiments, dipyridamole is administered by intravenous or intra-arterial bolus injection. In certain embodiments, dipyridamole is administered as an intravenous or intra-arterial bolus at a dosage of no more than 140 µg/kg, no more than 50 µg/kg, even no more than 40 µg/kg, and typically at a dosage of at least 14 µg/kg. For example, in some embodiments, dipyridamole is administered as an intravenous or intra-arterial bolus at a dosage of 23 to 60 µg/kg, such as 35 µg/kg or 40 µg/kg.

In various embodiments, dipyridamole is administered by intravenous infusion over 1 or 2 minutes.

In some of these embodiments, the adenosine receptor agonist administration is begun after completion of dipyridamole administration, such as between 30 seconds an 2 minutes after dipyridamole injection or infusion.

In a variety of embodiments, dipyridamole is administered in admixture with the adenosine receptor agonist by intravenous infusion over 2 to 6 minutes, such as for 4 minutes.

In typical embodiments, the adenosine receptor agonist is adenosine, administered by intravenous infusion at a dosage rate of about 35 µg/kg/min-100 µg/kg/min. In these embodiments, adenosine is administered at a dosage rate no more than about 100 µg/kg/min. In some embodiments, adenosine is administered at a dosage rate of no more than about 70 µg/kg/min, even no more than about 50 µg/kg/min. In exemplary embodiments, the adenosine receptor agonist is adenosine, administered by intravenous infusion at a dosage rate of at least about 35 µg/kg/min, even at least about 50 µg/kg/min. For example, in some embodiments, adenosine is administered by intravenous infusion at a rate of about 50 µg/kg/min to about 70 µg/kg/min, such as about 70 µg/kg/min.

In some embodiments, dipyridamole is administered intravenously and adenosine is administered intravenously.

In certain exemplary embodiments, the adenosine receptor agonist is adenosine, the total dose of dipyridamole is 23 to 40 µg/kg, and the dosage rate for adenosine is 50 to 70 µg/kg/min. For example, in some embodiments, the total dose of dipyridamole is 40 µg/kg and the dosage rate for adenosine is 70 µg/kg/min.

The method may further comprise the step of: assessing cardiac function. In some embodiments, assessing cardiac function includes parenteral administration of an isotope, and the isotope is administered after 2 minutes, when dipyridamole and the adenosine receptor agonist are administered sequentially, and after 2.5 minutes, after 2.55 minutes, after 2.6 minutes, after 2.65 minutes, after 2.75 minutes, after 2.8 minutes, after 2.85 minutes, after 2.9 minutes or after 2.95 minutes but before 3 minutes, when dipyridamole and the adenosine receptor agonist are administered concurrently. In some embodiments, isotope is administered at about 2.5-2.75 minutes after sequential administration of dipyridamole and the adenosine receptor agonist.

In a third aspect, pharmaceutical compositions comprising adenosine and dipyridamole are presented. The compositions comprise adenosine and dipyridamole in adenosine:dipyridamole weight ratios of about 2:1 to about 10:1, such as about 2:1 to about 4:1. In some embodiments, the ratio is about 7:1 or 8:1.

In various embodiments, adenosine and dipyridamole are present in amounts that permit adenosine to be administered at a dosage rate of 35 to 100 g/kg/min and dipyridamole to be administered at a dosage rate of 3.5 to 50 µg/kg/min.

The composition may be a sterile fluid, such as a sterile fluid suitable for parenteral administration, such as intravenous administration. In some embodiments, adenosine and dipyridamole are present at concentrations that permit direct intravenous administration, without dilution.

In various embodiments, adenosine and dipyridamole are present at concentrations that permit administration of adenosine at a dosage rate of 70 µg/kg/min and dipyridamole at a dosage rate of 8.75 to 10 µg/kg/min. In some embodiments, adenosine and dipyridamole are present at concentrations that permit administration of adenosine at a dosage rate of 50 µg/kg/min and dipyridamole at a dosage rate of 12.5 to 25 µg/kg/min.

In a range of embodiments of the pharmaceutical compositions here provided, the concentration of adenosine is about 1 to 10 mg/ml. Usefully, the concentration of adenosine is about 3 mg/ml or 4 mg/ml, even 5 mg/ml, or 7 mg/ml.

In certain embodiments, the concentration of dipyridamole is about 0.1 to 5 mg/ml, such as: 0.375 to 0.428 mg/ml; 0.5 to 0.571 mg/ml; 0.625 to 0.714 mg/ml; 0.75 to 0.857 mg/ml; and 0.875 to 1 mg/ml. The concentration may, for example, be 1 mg/ml.

In another aspect, unit dosage forms are provided that contain pharmaceutical compositions as above-described, comprising adenosine and dipyridamole.

In some embodiments, the unit dose contains about 2 to 50 ml of the pharmaceutical composition formulated as a sterile fluid, typically a sterile, nonpyrogenic, solution suitable for parenteral administration. In some embodiments, the unit dose contains about 2 ml, 3 ml, 4 ml, 7 ml, 8 ml or 14 ml.

In some embodiments, the unit dose contains about 5 to 60 mg of adenosine and about 0.5 to 30 mg of dipyridamole; the composition is a solid capable of sterile reconstitution in a physiologically acceptable solvent or solution.

In exemplary embodiments, for example, the unit dosage contains about 14 mg of adenosine and about 2 mg of dipyridamole, 21 mg of adenosine and about 3 mg of dipyridamole; about 28 mg of adenosine and about 4 mg of dipyridamole; about 35 mg of adenosine and about 5 mg of dipyridamole; about 42 mg of adenosine and about 6 mg of dipyridamole; about 56 mg of adenosine and about 8 mg of dipyridamole; about 20 mg of adenosine and about 5 to 10 mg of dipyridamole; about 30 mg of adenosine and about 7.5 to 15 mg of dipyridamole; about 40 mg of adenosine and about 10 to 20 mg of dipyridamole.

In a further aspect, unit doses of dipyridamole are provided. In various embodiments, dipyridamole is provided in solution at a concentration of about 0.1 to 5 mg/ml.

In certain embodiments, the dipyridamole concentration is usefully about 0.5 mg/ml. Among these embodiments are unit dosage forms that contain 3 mg dipyridamole in 6 ml; 4 mg dipyridamole in 8 ml; 5 mg dipyridamole in 10 ml; 6 mg dipyridamole in 12 ml; 8 mg dipyridamole in 16 ml. In some embodiments, the unit dose contains dipyridamole at a concentration between about 3 mg/ml and about 5 mg/ml, such as 3 mg/ml or 4 mg/ml, usefully in volumes of 1 ml or of 2 ml, providing unit dosage forms containing 6 mg dipyridamole in 2 ml and 8 mg dipyridamole in 2 ml.

In a further aspect, unit doses of adenosine are provided. The unit doses are formulated in sterile fluid composition, and the dose packaging permits sterile introduction of a second fluid in a volume at least 15% that of the adenosine composition. The second fluid usefully comprises dipyridamole.

In exemplary embodiments, the unit dose contains 21 mg adenosine in 6 ml; 28 mg adenosine in 6 ml; 42 mg adenosine in 12 ml; or 56 mg adenosine in 12 ml.

In some embodiments the unit dose may comprise adenosine at a concentration of about 4 mg/ml. In some embodiments, the unit dose contains 28 mg adenosine in 7 ml; 56 mg adenosine in 14 ml.

Also provided are kits. The kits comprise at least one unit dose of dipyridamole and at least one unit dose of adenosine. In some embodiments, the at least one unit dose of dipyridamole is a unit dose as above-described, and the unit dose of adenosine is a unit dose as above-described.

4. DETAILED DESCRIPTION

4.1 Overview

Although dipyridamole is believed to act indirectly by increasing adenosine concentration, and in clinical practice has a side effect profile similar to that of adenosine, I have now discovered that extremely low parenteral-subclinical doses of dipyridamole—on the order of 5% of the dose now used clinically in cardiac imaging studies—can potentiate the vasodilation effects of adjunctively administered adenosine without commensurate potentiation of adenosine's side effects. This permits adenosine to be used at reduced dosage to effect coronary vasodilation, e.g., for functional assessment of myocardial function, with equal or superior efficacy as compared to current protocols, yet with reduced side effects, of short duration.

In the first of two clinical studies reported in detail below (Example 1), the hemodynamic effects of administering dipyridamole and adenosine intravenously as a combined (albeit, sequentially administered) pharmacological stressor were compared to the effects of administering adenosine alone in 40 consecutive patients suffering from ischemic heart disease. Each patient served as his own control. Dipyridamole was administered as an intravenous bolus. Adenosine was administered immediately thereafter by continuous intravenous infusion for three minutes. Each of the two agents was administered at a dosage lower than its clinically preferred dosage when used as a single agent for myocardial perfusion imaging: dipyridamole at 4-6% of its single-agent total dose, adenosine at one half its single-agent dosage rate.

Effects were measured using noninvasive transthoracic doppler echocardiography (TTDE). The measured blood flow velocities (known as reflecting coronary blood flow values), whether peak or mean, were 1.5 to 4% lower in absolute values than those measured upon administration of adenosine alone at its standard dosage rate. However, these differences were not statistically significant ($p > 0.05$): there was no statistical difference between the current standard treatment—infusion of adenosine alone at 140 µg/kg/min—and sequential bolus administration of dipyridamole at 4-6% of its typical single-agent total dose followed by adenosine infusion at 70 µg/kg/min.

In addition, among the first series of 30 patients, three (3) patients received the adenosine infusion two minutes after the dipyridamole bolus, rather than immediately thereafter, and two (2) patients were injected with the two agents concurrently in the same infusion line using a "Y" connector. No differences were seen as compared to the sequential administration protocol.

A significant reduction was seen in the incidence of chest pain among the 40 patients in this study, as compared to the number reporting chest pain upon administration of adenosine alone at 140 µg/kg/min. In addition, the severity of the three main adverse side effects—chest pain, dyspnea, and flushing cumulated across all dipyridamole doses, was reduced by 31.6% with the sequential combination as compared to standard adenosine treatment. This decrease was statistically significant (p=0.001).

As reported in detail in Example 2, below, 27 patients have now been assessed in a subsequent Phase II study comparing dipyridamole-adenosine combination administration to adenosine alone (Adenoscan®, Astellas) as the pharmacologic stressor in coronary patients undergoing single photon emission computed tomography (SPECT) imaging studies.

Data from initial patients who participated in a preliminary dose-finding study demonstrated that either bolus intravenous administration of dipyridamole at 35 µg/kg over 20-30 seconds, followed by intravenous infusion of adenosine at 70 µg/kg/min (tested in 3 patients) or the concurrent administration of the two drugs at the same dosage (tested in 5 patients), provided images comparable to Adenoscan (adenosine at 140 µg/kg/min) in 7 consecutive patients, while under-scoring Adenoscan in one patient, but within the acceptable limits defined by the protocol. The combination stressor of 40 µg/kg dipyridamole followed by 70 µg/kg/min adenosine tested in 10 patients or their concurrent administration at the same dosage (adenosine 70 µg/kg/mn with dipyridamole 10 µg/kg/mn) tested in 9 patients showed equivalent, and sometimes better results, than Adenoscan in terms of imaging efficacy in 10 and 9 consecutive patients respectively.

Significant reduction in both the occurrence and the severity of chest pain with the dipyridamole-adenosine combination, as compared to adenosine alone, was observed, as was reduction in ST changes on EKG.

The data from these two studies demonstrate that the sequential bolus administration of dipyridamole at 28 to 40 µg/kg—well below the total dose infused when dipyridamole is used as a single agent stressor—followed by infusion of adenosine at 70 µg/kg/min (50% less than its usual dosage), is equally efficacious in providing coronary vasodilation for imaging studies, while causing fewer side effects. The data also demonstrate that dipyridamole and adenosine may be combined in a single infusion, over 4 minutes, to similar effect. Among the side effects reduced by the combination of the present invention are chest pain, and the risk of significant heart blockage.

Accordingly, described herein are methods, pharmaceutical compositions, unit dosage forms, and kits that exploit this discovery, combining adenosine with dipyridamole at dosages at which some of the most frequent side effects of both adenosine and dipyridamole, notably cardiac side effects, are significantly reduced, while maintaining optimal coronary vasodilation for the diagnosis of myocardial ischemia.

4.2 Methods of Effecting Coronary Vasodilation

In a first aspect, methods of effecting coronary vasodilation for cardiac diagnosis are provided.

In typical embodiments, the methods comprise parenterally administering dipyridamole and concurrently or sequentially thereafter parenterally administering an adenosine receptor agonist. Each of dipyridamole and the adenosine receptor agonist is administered at a dosage lower than that required for maximal coronary vasodilation when the respective agent is administered individually by identical parenteral route. Dipyridamole and the adenosine receptor agonist are administered in amounts, at weight ratios, and for a time, sufficient to achieve the desired therapeutic or diagnostic effect.

Programmable syringe pumps or micropumps, as are typical in clinical practice, are usefully employed to facilitate parenteral administration in precise dosage.

The route of parenteral administration is chosen based upon the desired clinical effect, as further described below. In certain embodiments, at least one of dipyridamole and the adenosine receptor agonist is administered by intravenous infusion. In other embodiments, at least one of dipyridamole and the adenosine receptor agonist is administered by intra-arterial infusion, such as intra-coronary infusion, or by intra-atrial infusion. In these latter embodiments, the active is administered at a lower rate, and at a lower dosage, than for intravenous infusion, as further described below. In yet other embodiments, at least one of the actives is administered as a perfusate.

In some embodiments, at least one of dipyridamole and the adenosine receptor agonist is infused over a period of time of at least 1 minute, typically at least 2 minutes, 3 minutes, 4 minutes, 5 minutes, even at least 6 minutes. As used herein, "continuous infusion" intends infusion over a period of at least 2 minutes.

In some embodiments, dipyridamole is administered by intravenous infusion at an infusion rate from 3.5 µg/kg/min to 50 µg/kg/min. All dosage ranges described herein include the upper and lower recited limits, and nonintegral intermediary values. Thus, in some embodiments, dipyridamole is infused at a rate of at least about 3.5 µg/kg/min, at least about 4 µg/kg/min, at least about 5 µg/kg/min, at least about 6 µg/kg/min, at least about 7 µg/kg/min, at least about 7.5 µg/kg/min, at least about 8 µg/kg/min, at least about 8.75 µg/kg/min, at least about 9 µg/kg/min, at least about 10 µg/kg/min, at least about 11 µg/kg/min, at least about 11.25 µg/kg/min, at least about 12 µg/kg/min, at least about 12.5 µg/kg/min, at least about 13 µg/kg/min, at least about 13.75 µg/kg/min, at least about 14 µg/kg/min, at least about 15 µg/kg/min, at least about 16 µg/kg/min, at least about 16.25 µg/kg/min, at least about 17 µg/kg/min, and at least about 17.5 µg/kg/min, at least about 18 µg/kg/min, at least about 19 µg/kg/min, at least about 20 µg/kg/min, at least about 21 µg/kg/min, at least about 22 µg/kg/min, at least about 23 µg/kg/min, at least about 24 µg/kg/min, at least about 25 µg/kg/min, at least about 26 µg/kg/min, at least about 27 µg/kg/min, at least about 28 µg/kg/min, at least about 29 µg/kg/min, at least about 30 µg/kg/min, at least about 31 µg/kg/min, at least about 32 µg/kg/min, at least about 33 µg/kg/min, at least about 34 µg/kg/min, at least about 35 µg/kg/min, at least about 36 µg/kg/min, at least about 37 µg/kg/min, at least about 38 µg/kg/min, at least about 39 µg/kg/min, at least about 40 µg/kg/min, at least about 41 µg/kg/min, at least about 42 µg/kg/min, at least about 43 µg/kg/min, at least about 44 µg/kg/min, at least about 45 µg/kg/min, at least about 46 µg/kg/min, at least about 47 µg/kg/min, at least about 48

μg/kg/min, at least about 49 μg/kg/min, at least about 50 μg/kg/min, with intermediate values permissible.

In some embodiments, dipyridamole is infused intravenously at a rate of no more than about 50 μg/kg/min, no more than about 49 μg/kg/min, no more than about 48 μg/kg/min, no more than about 47 μg/kg/min, no more than about 46 μg/kg/min, no more than about 45 μg/kg/min, no more than about 44 μg/kg/min, no more than about 43 μg/kg/min, no more than about 42 μg/kg/min, no more than about 41 μg/kg/min, no more than about 40 μg/kg/min, no more than about 39 μg/kg/min, no more than about 38 μg/kg/min, no more than about 37 μg/kg/min, no more than about 36 μg/kg/min, no more than about 35 μg/kg/min, no more than about 34 μg/kg/min, no more than about 33 μg/kg/min, no more than about 32 μg/kg/min, no more than about 31 μg/kg/min, no more than about 30 μg/kg/min, of no more than about 29 μg/kg/min, no more than about 28 μg/kg/min, no more than about 27 μg/kg/min, no more than about 26 μg/kg/min, no more than about 25 μg/kg/min, no more than about 24 μg/kg/min, no more than about 23 μg/kg/min, no more than about 22 μg/kg/min, no more than about 21 μg/kg/min, no more than about 20 μg/kg/min, no more than about 19 μg/kg/min, no more than about 18 μg/kg/min, no more than about 17.5 μg/kg/min, no more than about 17 μg/kg/min, no more than about 16.25 μg/kg/min, no more than about 16 μg/kg/min, no more than about 15 μg/kg/min, no more than about 14 μg/kg/min, no more than about 13.75 μg/kg/min, no more than about 13 μg/kg/min, no more than about 12.5 μg/kg/min, no more than about 12 μg/kg/min, no more than about 11.25 μg/kg/min, no more than about 11 μg/kg/min, no more than about 10 μg/kg/min, no more than about 9 μg/kg/min, no more than about 8.75 μg/kg/min, no more than about 8 μg/kg/min, no more than about 7.5 μg/kg/min, no more than about 7 μg/kg/min, no more than about 6 μg/kg/min, no more than about 5 μg/kg/min, no more than about 4 μg/kg/min, no more than about 3.5 μg/kg/min, with intermediate values permissible.

In some embodiments, dipyridamole is administered as a bolus, typically over a period of about 20-30 seconds.

In some of these embodiments, dipyridamole is administered as an intravenous bolus. In such embodiments, dipyridamole is administered at a dosage between 14 μg/kg to 14 μg/kg. In various embodiments, dipyridamole is administered intravenously as a bolus at a dosage between 28 μg/kg and 40 μg/kg.

Thus, in certain embodiments, dipyridamole is administered as an intravenous bolus at a dose of at least about 14 μg/kg, at least about 20 μg/kg, at least about 25 μg/kg, at least about 28 μg/kg, at least about 29 μg/kg, at least about 30 μg/kg, at least about 31 μg/kg, at least about 32 μg/kg, at least about 33 μg/kg, at least about 34 μg/kg, at least about 35 μg/kg, at least about 36 μg/kg, at least about 37 μg/kg, at least about 38 μg/kg, at least about 39 μg/kg, at least about 40 μg/kg, at least about 45 μg/kg, at least about 50 μg/kg, at least about 55 μg/kg, at least about 60 μg/kg, at least about 65 μg/kg, even at least about 70, 80, 90, 100, 110, 120, 130, even 140 μg/kg, with intermediate doses permissible.

In some embodiments, dipyridamole is administered intravenously as a bolus at a dosage of no more than about 140 μg/kg, 130 μg/kg, 120 μg/kg, 110 μg/kg, 100 μg/kg, 90 μg/kg, 80 μg/kg, 70 μg/kg, even no more than about 60 μg/kg, even no more than about 55 μg/kg, no more than about 50 μg/kg, no more than about 45 μg/kg, no more than about 40 μg/kg, no more than about 39 μg/kg, no more than about 38 μg/kg, no more than about 37 μg/kg, no more than about 36 μg/kg, no more than about 35 μg/kg, no more than about 34 μg/kg, no more than about 33 μg/kg, no more than about 32 μg/kg, no more than about 31 μg/kg, no more than about 30 μg/kg, no more than about 29 μg/kg, no more than about 28 μg/kg, no more than about 25 μg/kg/, no more than about 20 μg/kg/, no more than about 14 μg/kg, with intermediate values permissible.

When administered to a human being, the dosages of dipyridamole useful in the methods of the present invention can be expressed in μg by multiplying the dosage, expressed as μg/kg, by the weight of the individual. For example, for a human weighing 50 kg, the dosage of dipyridamole useful in the present methods can be expressed as ranging between 700 to 7,000 μg; for a human being weighing 60 kg, the dosage of dipyridamole can be expressed as ranging between 840 to 8,400 μg; for a human being weighing 75 kg, the dosage of dipyridamole can be expressed as ranging between 1,050 to 10, 500 μg; and for a human being weighing 100 kg, the dosage can be expressed as ranging between 1,400 to 14,000 μg.

In various embodiments, dipyridamole is infused intraarterially at an infusion rate of no more than about 0.07 μg/kg/min, no more than about 0.06 μg/kg/min, no more than about 0.05 μg/kg/min, no more than about 0.04 μg/kg/min, no more than about 0.03 μg/kg/min, no more than about 0.02 μg/kg/min, or no more than about 0.01 μg/kg/min, with intermediate values permissible.

In various embodiments, the adenosine receptor agonist is selected from the group consisting of adenosine, and adenosine donors (that is, compounds that can be metabolized to adenosine), including natural donors such as adenosine triphosphate (ATP), adenosine diphosphate (ADP), and adenosine monophosphate (AMP), each at approximately the same dosages as adenosine, and any synthetic molecule that is capable of being metabolized to adenosine, and pharmaceutically acceptable salts thereof.

Typically, adenosine is used. For convenience, its particular use will hereafter be described, without intending thereby to limit the described methods to use of adenosine as the adenosine receptor agonist.

In some embodiments, adenosine is administered by intravenous infusion at an infusion rate between 35 μg/kg/min to 100 μg/kg/min. Thus, in some embodiments, adenosine is infused at a rate of at least about 35 μg/kg/min, at least about 40 μg/kg/min, at least about 45 μg/kg/min, at least about 50 μg/kg/min, at least about 55 μg/kg/min, at least about 60 μg/kg/min, at least about 65 μg/kg/min, at least about 70 μg/kg/min, at least about 75 μg/kg/min, at least about 80 μg/kg/min, at least about 85 μg/kg/min, at least about 90 μg/kg/min, at least about 95 μg/kg/min, and at least about 100 μg/kg/min, with intermediate values permissible.

In various embodiments, adenosine is infused intravenously at a rate of no more than about 100 μg/kg/min, no more than about 95 μg/kg/min, no more than about 90 μg/kg/min, no more than about 85 μg/kg/min, no more than about 80 μg/kg/min, no more than about 75 μg/kg/min, no more than about 70 μg/kg/min, no more than about 65 μg/kg/min, no more than about 60 μg/kg/min, no more than about 55 μg/kg/min, no more than about 50 μg/kg/min, no more than about 45 μg/kg/min, no more than about 40 μg/kg/min, no more than about 35 μg/kg/min, with intermediate values permissible.

When administered to a human being, the dosage rate of adenosine can be expressed in μg/min by multiplying the dosage rate expressed in μg/kg/min by the weight of the individual. For example, for a human being weighing 50 μg, the dosage of adenosine useful in the practice of the present methods can be expressed as ranging between 1,750 to 5,000 μg/min; for a human being weighing 60 μg, the dosage rate of adenosine can be expressed as ranging between 2,100 to 6,000 μg/min; for a human being weighing 75 μg, the dosage of adenosine can be expressed as ranging between 2,625 to 7,500 µg/min; and for a human being weighing 100 kg, the dosage of adenosine can be expressed as ranging between 3,500 to 10,000 µg/min.

In some embodiments, adenosine is administered by intra-arterial infusion, such as intracoronary infusion, at an infusion rate about 200- to 400-fold lower than intravenous infusion. Thus, in some embodiments, adenosine is infused at a rate of at least about 0.50 µg/kg/min, at least about 0.45 µg/kg/min, at least about 0.40 µg/kg/min, 0.35 µg/kg/min, at least about 0.30 µg/kg/min, at least about 0.25 µg/kg/min at least about 0.20 µg/kg/min, at least about 0.15 µg/kg/min, at least about 0.10 µg/kg/min, with intermediate values permissible.

In various embodiments, adenosine is infused intra-arterially and in particular intracoronarily at an infusion rate of no more than about 0.10 µg/kg/min, no more than about 0.15 µg/kg/min, no more than about 0.20 µg/kg/min, no more than about 0.25 µg/kg/min, no more than about 0.30 µg/kg/min, no more than about 0.35 µg/kg/min, no more than about 0.40 µg/kg/min, no more than about 0.45 µg/kg/min, even no more than about 0.50 µg/kg/min, with intermediate values permissible.

In various embodiments, the methods presented herein comprise parenterally administering dipyridamole; and concurrently or sequentially thereafter parenterally administering an adenosine receptor agonist, such as adenosine, at an adenosine:dipyridamole (A:D) weight ratio of about 2:1 to about 10:1. In various embodiments, the methods comprise concurrently administering adenosine and dipyridamole at an adenosine:dipyridamole ratio of about 2:1 to about 10:1.

In some embodiments, the ratio is about 2:1, 3:1, 4:1, 5:1, 6:1, 7:1, 8:1, 9:1, even 10:1, with nonintegral ratios between 2:1 and 10:1 permissible. In certain embodiments, the methods comprise concurrent infusion of adenosine and dipyridamole at an A:D ratio of about 6:1 to 8:1, preferably about 7:1. For certain methods further described below, embodiments usefully comprise concurrent parenteral infusion of adenosine and dipyridamole at an A:D weight ratio of about 2:1 to 4:1.

In some embodiments, dipyridamole is administered by intra-coronary infusion: in such embodiments, dipyridamole is typically administered at an infusion rate which is about ⅐ that of adenosine, and between 0.01 to 0.07 µg/kg/min. Thus, in some embodiments, dipyridamole is infused intra-arterially at a rate of at least about 0.01 µg/kg/min, at least about 0.02 µg/kg/min at least about 0.03 µg/kg/min at least about 0.04 µg/kg/min at least about 0.05 µg/kg/min at least about 0.06 µg/kg/min at least about 0.07 µg/kg/min.

In various embodiments, dipyridamole is administered as an intravenous bolus, and adenosine is administered thereafter as an intravenous infusion.

In certain such embodiments, dipyridamole is administered over about 20-30 seconds, and adenosine is thereafter infused for about 2 to 6 minutes.

In these embodiments, the total dose of dipyridamole given intravenously as a bolus is typically between 1/16 to 1/24, e.g., 1/20 (5%), that of the total recommended standard dose when dipyridamole is used as a single agent (standard single agent dose: 0.56 mg-0.80 mg/kg). In these embodiments, the total dose of intravenously infused adenosine is typically 25% to 50% that of the total recommended standard dose when adenosine is used as a single agent (standard single agent dose: 0.84 mg/kg).

In typical embodiments, dipyridamole is administered as an IV bolus over 20-30 seconds at a dosage of 14 to 60 µg/kg, followed immediately (that is, as soon as clinically practicable, typically within about 5 to 30 seconds) by the infusion of adenosine at a dosage of 35 to 100 µg/kg/min for a period of 3 to 6 minutes. The duration of adenosine administration is determined by the chosen imaging methodology, as is well known in the art.

In some embodiments, an intravenous dipyridamole bolus of 28-40 µg/kg is followed immediately—that is, as soon as clinically practicable, typically within about 5 to 30 seconds—by intravenous infusion of adenosine at 50-70 µg/kg/min for 2 to 6 minutes. In certain embodiments, an IV dipyridamole bolus of 40 µg/kg is followed immediately by intravenous administration of adenosine at 70 µg/kg/min for 4 minutes.

In sequential administration embodiments, adenosine infusion may be delayed as long as 2-10 minutes after dipyridamole bolus, typically no more than 5 minutes after dipyridamole bolus.

In sequential administration embodiments, dipyridamole may be injected manually as a bolus via a syringe, although programmable administration (e.g., by micropump) is also possible. When administered by micropump, dipyridamole may be injected over 1 or to 2 minutes prior to adenosine infusion. Adenosine infusion is typically accomplished using a programmable device so as to ensure its measured delivery.

In some embodiments, dipyridamole and adenosine are administered concurrently.

In certain concurrent administration embodiments, dipyridamole and adenosine are in separate unit dosage forms, and are mixed prior to administration and infused together in a single composition.

For example, in some embodiments, a volume of dipyridamole corresponding to a dosage of 14 to 60 µg/kg is sampled and a volume of adenosine corresponding to a dosage of 35 to 100 µg/kg/min is similarly sampled and the two mixed in the same syringe. The mixture is then infused over 3 to 6 minutes. The duration of intravenous administration is determined by the chosen imaging methodology, as is well known in the art.

In some embodiments, a volume of dipyridamole corresponding to 28-40 µg/kg is sampled and a volume of adenosine corresponding to a dosage of 50 to 70 µg/kg/min is similarly sampled, and the two mixed in the same syringe. The mixture is then infused over 3 to 6 minutes. In certain embodiments, a volume of dipyridamole corresponding to 40 µg/kg is sampled and a volume of adenosine corresponding to a dosage of 70 µg/kg/min is similarly sampled and the two mixed in the same syringe. The mixture is then infused over 4 minutes. Thus, as is described further below, in another aspect, specific unit dosage forms of adenosine are provided, usefully copackaged with specific unit dosage forms of dipyridamole, so as to facilitate the sequential sampling and mixture of both actives in the same syringe.

In other embodiments, the total volume of the dipyridamole unit dosage form is injected into the adenosine vial and the two are mixed. Thus, as described below, in another aspect the invention provides unit dosage forms of adenosine packaged so as to permit the sterile introduction of an appropriate volume of dipyridamole.

In embodiments in which the two actives are in admixture in a single composition prior to administration, the volume to administer is usefully calculated using adenosine dose tables as reference.

In other embodiments, dipyridamole and adenosine are concurrently administered from separate compositions. Usefully, the two agents may be introduced into the same infusion line using a Y connector (at the same dosages as set forth above).

4.3 Methods of Pharmacological Stress Testing

Vasodilation that is achieved according to the above-described methods will often be used as a pharmacological stressor in cardiac stress tests. Accordingly, in certain embodiments, the methods further comprise the step of assessing cardiac function.

Any method suitable for assessing cardiac function in cardiac stress testing may be used.

In various embodiments, for example, assessing cardiac function includes use of one or more techniques selected from the group consisting of: electrocardiography, echography (M mode, two-dimensional, and three dimensional), echo-doppler, cardiac imaging, including planar (conventional) scintigraphy, single photon emission computed tomography (SPECT), dynamic single photon emission computed tomography (D-SPECT™ Cardiac Scan), positron emission tomography (PET), radionuclide angiography (first pass and equilibrium studies utilizing, e.g., technetium-99m-labeled red blood cells), nuclear magnetic resonance (NMR) imaging, perfusion contrast echocardiography, digital subtraction angiography (DSA), and ultrafast x-ray computed tomography (CINE CT).

SPECT and PET present certain advantages.

SPECT studies can be performed using any of the isotopes known to be suitable for such studies, such as thallium-201, technetium sestamibi, tetrofosmine. PET studies can be performed using any of the isotopes known to be suitable for such studies, such as for example rubidium-82, nitrogen-13, fluorine-18, carbon-11, boron-11, and oxygen-15.

Typically, isotope is injected during the infusion of adenosine, and imaging begins after the end of the infusion. In some embodiments, the isotope is administered no less than about 2.5 minutes after adenosine infusion has begun.

4.4 Pharmaceutical Compositions

In another aspect, pharmaceutical compositions that are useful in the above-described methods are provided.

In typical embodiments, the pharmaceutical composition comprises adenosine and dipyridamole in an adenosine:dipyridamole (A:D) weight ratio of about 2:1 to about 10:1, with intermediate (including nonintegral) values permissible. In certain embodiments in which adenosine is intended to be administered at 70 µg/kg/min, the ratio is usefully about 7:1, 8:1, 9:1 and 10:1, with intermediate and nonintegral ratios permissible. In other embodiments, in which adenosine is to be administered at 50 µg/kg/min or less, A:D ratios are usefully about 2:1, 3:1, and 4:1, with intermediate and nonintegral ratios between 2:1 and 4:1 permissible. For certain clinical methods, the composition usefully comprises adenosine and inosine at an A:D weight ratio of about 7:1.

In certain embodiments, the pharmaceutical composition is suitable for intravenous, intra-atrial, or intra-arterial infusion.

The composition may, for example, be in the form of a sterile, nonpyrogenic, fluid composition.

In typical fluid embodiments, the concentration of adenosine is at least about 1 mg/ml, 2 mg/ml, 3 mg/ml, 4 mg/ml and possibly 5 mg/ml, with intermediate, nonintegral, values permissible. These embodiments typically have a pH of about 3.5 to about 8. In other typical fluid embodiments with readily a lower pH (e.g., pH 2-3.5), adenosine concentration can be higher, even at least about 5 mg/ml, 6 mg/ml, 7 mg/ml, 8 mg/ml, 9 mg/ml and even 10 mg/ml, with intermediate, nonintegral, values permissible. In typical pharmaceutical composition embodiments, adenosine is present at a concentration of about 3 mg/ml, 4 mg/ml, 5 mg/ml, or 7 mg/ml.

In various fluid embodiments, the concentration of dipyridamole is at least about 0.1 mg/ml, and may usefully be as high as 2.5 mg/ml, and even 5 mg/ml. The concentration may, in certain embodiments, be at least about 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1 mg/ml, or more, including, e.g., 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2 mg/ml, 2.1 mg/ml, 2.2 mg/ml, 2.3 mg/ml, or 2.4 mg/ml, 2.5 mg/ml, 3 mg/ml, 3.5 mg/ml, 4 mg/ml, 4.5 mg/ml, 5 mg/ml, with intermediate and nonintegral values permissible (e.g., 0.43, 0.57, 0.71 or 0.86 mg/ml).

In certain embodiments, the composition comprises adenosine at a concentration of about 3 mg/ml, and dipyridamole at a concentration of about 0.375-0.428 mg/ml (A:D ratios of 8:1 and 7:1), which may be rounded to 0.38-0.43 mg/ml. In one embodiment, for example, the composition comprises adenosine at a concentration of about 3 mg/ml and dipyridamole at a concentration of about 0.43 mg/ml (ratio 7:1). In another embodiment, the composition comprises adenosine at a concentration of about 4 mg/ml and dipyridamole at a concentration of about 0.5-0.57 mg/ml (ratios of about 8:1 to 7:1). In another embodiment, the composition comprises adenosine at a concentration of about 5 mg/ml and dipyridamole at a concentration of about 0.62-0.71 mg/ml (ratios of 8:1 and 7:1). In another embodiment the composition comprises adenosine at a concentration of about 6 mg/ml and dipyridamole at a concentration of about 0.86 mg/ml (ratio 7:1). In another embodiment, the composition comprises adenosine at a concentration of about 7 mg/ml and dipyridamole at a concentration of about 1 mg/ml (ratio 7:1), and so on, up to adenosine concentrations as high as 10 mg/ml.

In other embodiments, the composition is dry, and suitable for reconstitution prior to infusion by addition of a sterile fluid into which both dipyridamole and adenosine are readily solubilized. Usefully, the composition comprises adenosine and dipyridamole in amounts suitable to permit reconstitution in the enclosing vessel to the adenosine and dipyridamole concentrations above-described.

Whether fluid or dry, the pharmaceutical composition may further comprise carriers and excipients suitable for intravenous, intra-atrial, or intra-arterial administration, as are well known in the art. Among such excipients are those used in currently approved dipyridamole and adenosine compositions, such as tartaric acid, hydrochloric acid and polyethylene glycol (macrogol 600). Others are permissible, such as, for example, mannitol. See, http://www.adenosin.com/en/en_SPC_05.pdf (Item Development AB, 2005), incorporated herein by reference. See also, *Remington: The Science and Practice of Pharmacy*, 21$^{st}$ ed. (2005), Lippincott Williams & Wilkins (ISBN: 0781746736), incorporated herein by reference.

The compositions may further comprise additional actives, and in some embodiments, may further comprise contrast agents, including ultrasound and MRI contrast agents.

In embodiments intended for continuous intravenous infusion in the methods above-described, adenosine is typically present in the pharmaceutical composition at a concentration, or in a weight amount, that permits adenosine to be infused at a rate between about 35 µg/kg/min to about 100 µg/kg/min.

In some of these embodiments, adenosine is present in an amount that permits infusion at a rate of at least about 35 µg/kg/min, at least about 40 µg/kg/min, at least about 45 µg/kg/min, at least about 50 µg/kg/min, at least about 55

μg/kg/min, at least about 60 μg/kg/min, at least about 65 μg/kg/min, at least about 70 μg/kg/min, at least about 75 μg/kg/min, at least about 80 μg/kg/min, at least about 85 μg/kg/min, at least about 90 μg/kg/min, at least about 95 μg/kg/min, and at least about 100 μg/kg/min, with intermediate and nonintegral values permissible.

In some embodiments, adenosine is present in the composition in an amount that permits infusion at a rate of no more than about 100 μg/kg/min, no more than about 95 μg/kg/min, no more than about 90 μg/kg/min, no more than about 85 μg/kg/min, no more than about 80 μg/kg/min, no more than about 75 μg/kg/min, no more than about 70 μg/kg/min, no more than about 65 μg/kg/min, no more than about 60 μg/kg/min, no more than about 55 μg/kg/min, no more than about 50 μg/kg/min, no more than about 45 μg/kg/min, no more than about 40 μg/kg/min, no more than about 35 μg/kg/min, with intermediate and nonintegral values permissible.

In embodiments intended for continuous intravenous infusion, dipyridamole is typically present in the pharmaceutical composition at a concentration, or in a weight amount, that permits dipyridamole to be infused at a rate between about 3.5 μg/kg/min to 50 μg/kg/min.

In some of these embodiments, dipyridamole is present in an amount that permits infusion at a rate of at least about 3.5 μg/kg/min, at least about 4 μg/kg/min, at least about 5 μg/kg/min, at least about 6 μg/kg/min, at least about 7 μg/kg/min, at least about 7.5 μg/kg/min, at least about 8 μg/kg/min, at least about 8.75 μg/kg/min, at least about 9 μg/kg/min, at least about 9.25 μg/kg/min, at least about 9.50 μg/kg/min at least about 10 μg/kg/min, at least about 11 μg/kg/min, at least about 11.25 μg/kg/min, at least about 12 μg/kg/min, at least about 12.5 μg/kg/min, at least about 13 μg/kg/min, at least about 13.75 μg/kg/min, at least about 14 μg/kg/min, at least about 15 μg/kg/min, at least about 16 μg/kg/min, at least about 16.25 μg/kg/min, at least about 17 μg/kg/min, and at least about 17.5 μg/kg/min, at least about 18 μg/kg/min, at least about 19 μg/kg/min, at least about 20 μg/kg/min, at least about 21 μg/kg/min, at least about 22 μg/kg/min, at least about 23 μg/kg/min, at least about 24 μg/kg/min, at least about 25 μg/kg/min, at least about 26 μg/kg/min, at least about 27 μg/kg/min, at least about 28 μg/kg/min, at least about 29 μg/kg/min, at least about 30 μg/kg/min, at least about 31 μg/kg/min, at least about 32 μg/kg/min, at least about 33 μg/kg/min, at least about 34 μg/kg/min, at least about 35 μg/kg/min, at least about 36 μg/kg/min, at least about 37 μg/kg/min, at least about 38 μg/kg/min, at least about 39 μg/kg/min, at least about 40 μg/kg/min, at least about 41 μg/kg/min, at least about 42 μg/kg/min, at least about 43 μg/kg/min, at least about 44 μg/kg/min, at least about 45 μg/kg/min, at least about 46 μg/kg/min, at least about 47 μg/kg/min, at least about 48 μg/kg/min, at least about 49 μg/kg/min, at least about 50 μg/kg/min, with intermediate and nonintegral values permissible.

In some embodiments, dipyridamole is present in the composition in an amount that permits intravenous infusion at a rate of no more than about 50 μg/kg/min, no more than about 49 μg/kg/min, no more than about 48 μg/kg/min, no more than about 47 μg/kg/min, no more than about 45 μg/kg/min, no more than about 44 μg/kg/min, no more than about 43 μg/kg/min, no more than about 42 μg/kg/min, no more than about 41 μg/kg/min, no more than about 40 μg/kg/min, no more than about 39 μg/kg/min, no more than about 38 μg/kg/min, no more than about 37 μg/kg/min, no more than about 36 μg/kg/min, no more than about 35 μg/kg/min, no more than about 34 μg/kg/min, no more than about 33 μg/kg/min, no more than about 32 μg/kg/min, no more than about 31 μg/kg/min, no more than about 30 μg/kg/min, of no more than about 29 μg/kg/min, no more than about 28 μg/kg/min, no more than about 27 μg/kg/min, no more than about 26 μg/kg/min, no more than about 25 g/kg/min, no more than about 24 μg/kg/min, no more than about 23 μg/kg/min, no more than about 22 μg/kg/min, no more than about 21 μg/kg/min, no more than about 20 μg/kg/min, no more than about 19 μg/kg/min, no more than about 18 μg/kg/min, no more than about 17.5 μg/kg/min, no more than about 17 μg/kg/min, no more than about 16.25 μg/kg/min, no more than about 16 μg/kg/min, no more than about 15 μg/kg/min, no more than about 14 g/kg/min, no more than about 13.75 μg/kg/min, no more than about 13 μg/kg/min, no more than about 12.5 μg/kg/min, no more than about 12 μg/kg/min, no more than about 11.25 μg/kg/min, no more than about 11 μg/kg/min, no more than about 10 μg/kg/min, no more than about 9.25 μg/kg/min, no more than about 9.50 μg/kg/min no more than about 9 μg/kg/min, no more than about 8.75 μg/kg/min, no more than about 8 μg/kg/min, no more than about 7.5 μg/kg/min, no more than about 7 μg/kg/min, no more than about 6 μg/kg/min, no more than about 5 μg/kg/min, no more than about 4 μg/kg/min, no more than about 3.5 μg/kg/min, with intermediate and nonintegral values permissible

4.5 Unit Dosage Forms

4.5.1 Dipyridamole:Adenosine Combined Compositions

The pharmaceutical compositions described herein are usefully packaged in a unit dosage form adapted for use in the methods above-described.

In embodiments in which the pharmaceutical composition is in the form of a liquid suitable for parenteral infusion, the composition may, for example, be packaged in volumes of 2-50 ml. Convenient unit dosage forms contain 2 to 14 ml, typically 2, 3, 4, 5, 6, 7, 8, or 14 ml. Unit dosage forms containing volumes as low as 1 ml, and unit dosage forms containing higher volumes, such as 15 or 20 ml, are also possible. Intermediate and nonintegral volumes are permissible.

Table 1 below lists certain useful unit dosage form embodiments of the adenosine:dipyridamole pharmaceutical compositions herein described.

TABLE 1

| Adenosine concentration (mg/ml) | Volume (ml) | Total amount of adenosine per dosage unit (mg) | Maximal patient weight (kgs) | Total amount of dipyridamole (A:D ratio 7:1) (mg) |
|---|---|---|---|---|
| 3 | 7 | 21 | 75 | 3 |
|  | 14 | 42 | 150 | 6 |
| 4 | 7 | 28 | 100 | 4 |
|  | 14 | 56 | 200 | 8 |

TABLE 1-continued

| Adenosine concentration (mg/ml) | Volume (ml) | Total amount of adenosine per dosage unit (mg) | Maximal patient weight (kgs) | Total amount of dipyridamole (A:D ratio 7:1) (mg) |
|---|---|---|---|---|
| 5 | 7 | 35 | 125 | 5 |
| 6 | 7 | 42 | 150 | 6 |
| 7 | 2 | 14 | 50 | 2 |
|   | 3 | 21 | 75 | 3 |
|   | 4 | 28 | 100 | 4 |
|   | 5 | 35 | 125 | 5 |
|   | 6 | 42 | 150 | 6 |
|   | 8 | 56 | 200 | 8 |

Thus, in some embodiments, the unit dosage form usefully contains 14 mg of adenosine and 2 mg of dipyridamole in 2 ml; 21 mg of adenosine and 3 mg of dipyridamole in 3 or 7 ml; 28 mg of adenosine and 4 mg of dipyridamole in 4 or 7 ml; 35 mg of adenosine and 5 mg of dipyridamole in 5 or 7 ml; 42 mg of adenosine and 6 mg of dipyridamole in 6 or 7 ml; 56 mg of adenosine and 8 mg of dipyridamole in 8 or 14 ml.

Various embodiments usefully package 9 mg or 12 mg adenosine respectively in 3 ml or 4 ml for light weight patients (e.g., children). Other embodiments usefully package 20 mg adenosine in 5 ml total volume (20 mg/5 ml), 24 mg in 6 ml total volume (24 mg/6 ml), and 25 mg in 5 ml total volume (25 mg/5 ml). Various unit dose embodiments of the pharmaceutical compositions described herein contain 30 mg adenosine in a total volume of 6 ml (30 mg/6 ml), 30 mg/1 ml, or 32 mg/8 ml. Other unit dose embodiments usefully contain adenosine at 36 mg/9 ml, 40 mg/10 ml, 40 mg/8 ml, 44 mg/1 1 ml, 45 mg/15 ml and 50 mg/10 ml.

In certain embodiments, the unit dosage form contains, in a total of 10 ml, 30 mg of adenosine and 3 to 5 mg of dipyridamole, with intermediate and nonintegral amounts of dipyridamole permissible (e.g., 3.75 mg or 4.28 mg, for A:D ratios of 8:1 and 7:1). In other embodiments, a 6 ml vial or ampule contains 24 mg of adenosine with 3 mg of dipyridamole (ratio 8:1). In other embodiments, an 8 ml vial or ampule will usefully contain 32 mg of adenosine with 3.2 to 5.3 mg of dipyridamole, with intermediate and nonintegral amounts of dipyridamole permissible (e.g., 4 mg to 4.57 mg, for ratios of 8:1 and 7:1).

The container for unit dosage embodiments is typically adapted for use with standard intravenous infusion sets.

In other embodiments, the unit dosage form contains adenosine and dipyridamole as solids suitable for reconstitution.

Whether liquid or dry, the unit dosage form is typically sterile and nonpyrogenic.

4.5.2 Dipyridamole Unit Dosage Forms

In typical embodiments of the methods herein described, dipyridamole is administered at about 5% of the dose at which it is currently administered as a single agent. Accordingly, in another aspect, the invention provides novel unit dosage forms of dipyridamole.

Convenient unit dosage forms of dipyridamole (as single active) are vials, ampules, or prefilled syringes, usefully with 0.1 ml graduations, containing dipyridamole at a concentration of 0.5 mg/ml. At a dipyridamole dose of 35-40 g/kg, a 5 mg/10 ml vial, ampule, or prefilled syringe is sufficient for almost all clinical needs, and is convenient for immediate and accurate dose adjustment. Also useful are unit dose forms of dipyridamole containing 4 mg/8 ml; 3.5 mg/7 ml; 3 mg/6 ml; 5 mg/1 ml; 6 mg/12 ml and 8 mg/16 ml.

Unit dosage forms containing dipyridamole at a concentration of 1 mg/ml—for example, unit dosage forms containing 6 mg dipyridamole in 6 ml, 5 mg/5 ml, 4 mg/4 ml, 3 mg/3 ml—also find use, but fine tuning the dose may be more difficult at this higher concentration. In these embodiments, adjustment is optimally obtained after dilution of dipyridamole, e.g., in saline solution.

Preparations with dipyridamole concentrations over 1 mg/ml, such as 2 mg/ml, 2.5 mg/ml, 3 mg/ml, 3.5 mg/ml, 4 mg/ml, 4.5 mg/ml, even 5 mg/ml are feasible, and are particularly convenient if it is intended to mix the whole of the dipyridamole unit dose into the adenosine unit dose, prior to administration. In this case, the 2 mg/ml, 3 mg/ml, 4 mg/ml, 5 mg/ml, 6 mg/2 ml or 8 mg/2 ml unit dosage forms (or prefilled syringes) are particularly useful.

In other embodiments, dipyridamole unit dosage forms contain dipyridamole at a lower concentration, such as 0.1 mg/ml. Usefully, such unit dosage forms contain 6 mg dipyridamole in 60 ml (6 mg/60 ml), 5 mg/50 ml, 4 mg/40 ml, and 3 mg/30 ml. Dipyridamole preparations at a concentration of 0.2, 0.3, and 0.4 mg/ml are also permissible.

4.5.3 Adenosine Unit Dosage Forms

As described above, in some embodiments, dipyridamole and adenosine are usefully provided in separate pharmaceutical compositions, and then combined prior to administration. In some of these embodiments, a dipyridamole composition is usefully introduced into a unit dose of adenosine, and the combined composition then administered.

Thus, unit dosage forms of adenosine are provided, in which adenosine is formulated in sterile fluid composition, and in which the dose packaging permits sterile introduction of a second fluid in a volume at least 15% that of the adenosine composition.

Adenosine may be present at any of the concentrations at which it is present in the pharmaceutical compositions above-described—e.g., usefully from 1 mg/ml to 5 mg/ml—either as directly packaged, or as thereafter will achieved upon introduction of an appropriate amount of dipyridamole composition.

For example, in one embodiment, an adenosine unit dosage form contains 21 mg adenosine in 6 ml (21 mg/6 ml). This will reconstitute to a desired 21 mg adenosine/7 ml (3 mg/ml adenosine) composition upon introduction of 1 ml of 3 mg/ml dipyridamole (e.g., the entirety of a unit dose of dipyridamole containing 1 ml dipyridamole at 3 mg/ml). In another embodiment, an adenosine unit dosage form contains 42 mg/12 ml. This will reconstitute to a desired 42 mg/14 ml (3 mg/ml) adenosine upon introduction of a 6 mg/2 ml dipyridamole unit dose. In another embodiment, the adenosine unit dosage form contains 28 mg adenosine/6 ml, which will reconstitute to 28 mg/7 ml (4 mg/ml adenosine) upon introduction of a 4 mg/ml dipyridamole unit dose. In another embodiment, the adenosine unit dosage form contains 56 mg adenosine/12 ml, which will reconstitute to 56 mg/14 ml (4 mg/ml adenosine) upon introduction of an 8 μg/2 ml dipyridamole unit dose. In another embodiment, the adenosine unit dosage form contains 28 mg/3 ml or 35 mg/4 ml which will reconstitute to 28 mg/4 ml and 35 mg/5 ml upon introduction of a 4 or 5 mg/ml dipyridamole unit dose respectively (7 mg/ml adenosine). In another embodiment, the adenosine unit dosage form contains 42 mg/4 ml or 56 mg/6 ml which will reconstitute to 42 mg/6 ml and 56 mg/8 ml upon introduction of a 6 mg/2 ml or 8 mg/2 ml dipyridamole unit dose respectively (7 mg/ml adenosine). The following table summarizes exemplary unit dosage forms.

TABLE 2

| Initial adenosine vial volume (ml) | Volume (ml) of dipyridamole solution added to each adenosine vial | Final adenosine vial (ml) volume after addition of dipyridamole | Final adenosine concentration (mg/ml) | Total amount of adenosine per unit dosage form (mg) | Total amount of dipyridamole (A:D ratio 7:1) (mg) | Maximal patient's weight covered by the composition (kgs) |
|---|---|---|---|---|---|---|
| 6 | 1 | 7 | 3 | 21 | 3 | 75 |
| 12 | 2 | 14 | 3 | 42 | 6 | 150 |
| 6 | 1 | 7 | 4 | 28 | 4 | 100 |
| 12 | 2 | 14 | 4 | 56 | 8 | 200 |
| 3 | 1 | 4 | 7 | 28 | 4 | 100 |
| 4 | 1 | 5 | 7 | 35 | 5 | 125 |
| 4 | 2 | 6 | 7 | 42 | 6 | 150 |
| 6 | 2 | 8 | 7 | 56 | 8 | 200 |

In certain embodiments, dipyridamole and adenosine are sequentially sampled from separate unit dosage forms, and mixed in the same syringe. In these embodiments, convenient adenosine unit dosage forms are 28 mg of adenosine in 7 ml and 56 mg of adenosine in 14 ml (4 mg/ml adenosine).

Typically, dosing and sampling are thereafter determined according to adenosine tables, and not dipyridamole tables.

4.6 Kits

In another aspect, kits are provided in which one or more unit doses of dipyridamole, such as those above-described, are packaged with one or more unit doses of adenosine, such as those above-described. Typically, the kit will comprise an equal number of dipyridamole and adenosine doses.

In some embodiments, the unit dose of dipyridamole is packaged in a pre-packed syringe, and the adenosine unit dose is packaged as a vial with an injection port, such as a septum, permitting sterile introduction of dipyridamole into the adenosine dose.

In various embodiments, the kit further includes one or more of an adenosine dosage table, one or more needles, diluent, and infusion sets.

5. EXAMPLES

5.1 Example 1

The effects of administering dipyridamole and adenosine intravenously as a combined (albeit, sequentially administered) pharmacological stressor were compared to the effects of administering adenosine alone in 40 consecutive patients suffering from ischemic heart disease. In the combined administration, each of the two agents was administered at a dosage lower than its clinically preferred dosage when used as a single agent for myocardial perfusion imaging. Effects were measured using noninvasive transthoracic doppler echocardiography (TTDE).

Primary efficacy end-points were peak and mean diastolic flow velocities (measured as reflecting coronary blood flow values). The secondary end-point was patient tolerance to the procedure. The protocol was designed as follows.

Forty (40) consecutive patients suffering from ischemic heart disease were enrolled. Each patient served as his own control.

Adenosine was administered by IV infusion for three minutes at the standard single-agent infusion rate of 140 μg/kg/min.

After a stabilization period of five minutes, patients then received an IV injection of dipyridamole at a total dose of either 23 μg/kg, 28 μg/kg, or 35 μg/kg, administered as a bolus over about 20-30 seconds. These total doses are between about 4-6% of the lowest single-agent total dose of dipyridamole (i.e., 0.56 mg/kg, infused over a total of 4 minutes).

The bolus injection of dipyridamole was followed immediately by an IV infusion of adenosine at 70 μg/kg/min for 3 minutes. This dose is half the standard single-agent dosage rate of 140 μg/kg/min.

Blood flow velocity was measured in the left anterior descending coronary artery (LAD) at four time points: (i) before initial adenosine infusion (spontaneous flow at rest), (ii) during the initial 140 μg/kg/min adenosine infusion, (iii) before the sequential administration of dipyridamole and adenosine (during the stabilization period), and (iv) during the 70 μg/kg/min adenosine infusion, subsequent to dipyridamole bolus injection.

Results are given in Tables 3-6. Abbreviations used in the table are defined below:

ADE: adenosine alone at 140 μg/kg/min

SC: sequential combination of dipyridamole followed by adenosine at 70 μg/kg/min PV: peak velocity (cm/sec)

MV: mean velocity (cm/sec)

max: velocity under stress conditions min: velocity at rest (under basal conditions)

( ): standard deviation

D %: velocity differential (peak or mean), as percentage of maximum peak or mean velocity Table 3 presents results comparing dipyridamole 28 μg/kg IV bolus (over 20-30 seconds) followed by adenosine infusion at 70 μg/kg/min ("DIP5" sequential combination) as compared to adenosine infusion alone at the standard single-agent dose of 140 μg/kg/min, in 30 patients.

TABLE 3

| | Peak velocity ADE | | Peak velocity SC | | Mean velocity ADE | | Mean velocity SC | |
|---|---|---|---|---|---|---|---|---|
| | Max | Min | Max | Min | Max | Min | Max | Min |
| Mean (s.d.) | 82.6 (20.7) | 30.6 (8.5) | 81 (21) | 30.6 (9.6) | 61.4 (15.1) | 23.1 (6.1) | 60.2 (15.3) | 22.9 (7.3) |
| Max velocity differential | PV: 82.6 − 81 = 1.6 | | | | MV: 61.4 − 60.2 = 1.2 | | | |
| Max velocity differential (D %) | 1.9% | | | | 1.9% | | | |
| P value | 0.217 | | | | 0.201 | | | |

Table 4 presents results comparing dipyridamole (35 μg/kg) bolus (administered over 20-30 seconds), followed by adenosine, administered by infusion at a rate of 70 μg/kg/min ("DIP4" sequential combination) as compared to adenosine infusion alone at the standard single-agent dose of 140 μg/kg/min, in 5 patients.

TABLE 4

| | Peak velocity ADE | | Peak velocity SC | | Mean velocity ADE | | Mean velocity SC | |
|---|---|---|---|---|---|---|---|---|
| | Max | Min | Max | Min | Max | Min | Max | Min |
| Mean (s.d.) | 80 (22.3) | 28 (7.4) | 78.8 (15.3) | 28 (7.7) | 60.4 (15.5) | 22.2 (5) | 57.8 (14.4) | 23 (5.7) |
| Max velocity differential | PV: 80 − 78.8 = 1.2 | | | | MV: 60.4 − 57.8 = 2.6 | | | |
| Max velocity differential (D %) | 1.5% | | | | 4.3% | | | |
| P value | 0.863 | | | | 0.448 | | | |

Table 5 presents results comparing dipyridamole (23 μg/kg), administered as a bolus over 20-30 seconds, followed by adenosine, administered by infusion at a rate of 70 μg/kg/min ("DIP6" sequential combination) as compared to adenosine infusion alone at the standard single-agent dose of 140 μg/kg/min, in 5 patients.

TABLE 5

| | Peak velocity ADE | | Peak velocity SC | | Mean velocity ADE | | Mean velocity SC | |
|---|---|---|---|---|---|---|---|---|
| | Max | Min | Max | Min | Max | Min | Max | Min |
| Mean (s.d.) | 107 (36.5) | 37.6 (12.1) | 105.4 (34.3) | 38.6 (16.5) | 80.2 (25.4) | 28.2 (11.1) | 79.2 (24.2) | 30 (14.7) |
| Max velocity differential | PV: 107 − 105.4 = 1.6 | | | | MV: 80.2 − 79.2 = 1 | | | |
| Max velocity differential (D %) | 1.5% | | | | 1.2% | | | |
| P value | 0.842 | | | | 0.771 | | | |

Table 6 presents results cumulated from all 40 patients:

TABLE 6

|  | Peak velocity ADE | | Peak velocity SC | | Mean velocity ADE | | Mean velocity SC | |
| --- | --- | --- | --- | --- | --- | --- | --- | --- |
|  | Max | Min | Max | Min | Max | Min | Max | Min |
| Mean (s.d.) | 85.3 (24) | 31.2 (9) | 83.8 (23.3) | 31.3 (10.5) | 63.6 (17.3) | 23.7 (6.8) | 62.3(17.3) | 23.7 (8.4) |
| Max velocity differential | | | PV: 85.3 − 83.8 = 1.5 | | | | MV: 63.6 − 62.3 = 1.3 | |
| Max velocity differential (D %) | | | 1.75% | | | | 2% | |
| P value | | | 0.314 | | | | 0.109 | |

The measured blood flow velocities, whether peak or mean, were 3 to 4% lower, in absolute values, than those of adenosine alone (see Tables 3 to 6). However, these differences were not statistically significant (all P values >0.05): there was no statistical difference between the standard treatment infusion of adenosine alone at 140 µg/kg/min—and sequential bolus administration of dipyridamole (at 4-6% its typical single-agent total dose) followed by adenosine at 70 µg/kg/min, whether assessed separately for each of the three tested dipyridamole doses (Tables 3-5), or cumulated across all dipyridamole doses (Table 6).

Table 7 shows the number and frequency of occurrence among all 40 patients of the three adverse events most commonly observed in clinical practice upon administration of adenosine alone at 140 µg/kg/min: chest pain, dyspnea, and flushing

TABLE 7

| Adverse event | ADE # patients reporting events (frequency) | All SC (DIP 4/5/6) # patients reporting events (frequency) | % reduction |
| --- | --- | --- | --- |
| Chest pain | 9 (22.5%) | 5 (12.5%) | −44% |
| Dyspnea | 20 (50%) | 18 (45%) | slight |
| Flushing | 21 (52.5%) | 17 (42.5%) | slight |

Table 8 presents descriptive statistics and analysis of the mean global visual analogue scale (VAS) score for the three main adverse events (each one being scored from 0 to 10 with a total score of 30). VAS scores provide a measure of patient self-assessment of pain intensity/discomfort.

TABLE 8

|  |  | n | Mean | SD |
| --- | --- | --- | --- | --- |
| Group DIP4 | ADE | 5 | 5.4 | 1.949 |
|  | SC | 5 | 3 | 3.742 |
| Group DIP5 | ADE | 30 | 5.95 | 3.705 |
|  | SC | 30 | 4.383 | 3.38 |
| Group DIP6 | ADE | 5 | 8.2 | 1.095 |
|  | SC | 5 | 4.4 | 2.408 |

Although not tabulated in Table 8, the severity of the three main adverse symptoms, cumulated across all dipyridamole doses, was reduced by 31.6% with the sequential combination as compared to adenosine alone. This decrease was statistically significant (p=0.001). No difference was observed as among the different doses of dipyridamole: all sequential combinations reduced mean severity on the VAS of each of the three main adverse symptoms, as compared to adenosine alone at 140 µg/kg/min.

As shown in Table 7 the number (and frequency) of adverse events related to the stimulation of A1 receptors, mainly chest pain, was reduced by 44% and its severity (not shown) decreased by 60% with the sequential combination treatment as compared to adenosine alone. The number (and frequency) of adverse events related to the stimulation of A2a receptors, mainly dyspnea and flushing, did not decrease. However their severity (not shown) decreased by 24 and 38% respectively, with the sequential combination compared to adenosine alone.

The mean coronary flow reserve (ratio of maximal-stimulated coronary blood flow "CBF" to baseline-resting CBF equivalent to peak and mean blood flow velocities ratios) of the 40 patients enrolled in the study was above 2, which indicates that the observed reduction in side effects with sequential treatment was drug dependent, and not flawed by the ischemic status of the studied population.

Although not shown in the tabular data, EKG was not significantly different with the sequential combination treatment as compared to standard single-agent adenosine, and remained unchanged in all the patients. Vital signs (heart rate, systolic and diastolic blood pressures) changed similarly with the two methods. However, the heart rate increase and blood pressures decreases were less pronounced with the sequential combination than with adenosine alone.

It should be noted that in the first series of 30 patients (DIP5 group), three (3) patients received the adenosine infusion 2 minutes after the dipyridamole bolus, and two (2) patients were injected the two agents (dipyridamole and adenosine) concurrently in the same infusion line using a "Y" connector. These two modalities appeared equally effective and as effective as the immediate sequential administration protocol.

In a first control experiment, 5 patients were treated according to a modification of the experimental protocol, in which the initial adenosine infusion at 140 µg/kg/min was followed by a five (5) minute stabilization period, and thereafter by a second, single-agent, adenosine infusion at 140 µg/kg/min, without the use of dipyridamole. Results are shown in Table 9. Abbreviations used in the table are defined below:

PV: peak velocity (cm/sec)
MV: mean velocity (cm/sec)
max: velocity under stress conditions
min: velocity at rest (under basal conditions)
ADE1: first adenosine infusion
ADE2: second adenosine infusion

TABLE 9

| Patient ID | PV-ADE1 Max | PV-ADE1 Min | PV-ADE2 Max | PV-ADE2 Min | MV-ADE1 Max | MV-ADE1 Min | MV-ADE2 Max | MV-ADE2 Min |
|---|---|---|---|---|---|---|---|---|
| MART | 68 | 34 | 60 | 31 | 49 | 25 | 45 | 23 |
| LIEN | 65 | 23 | 66 | 22 | 48 | 17 | 48 | 16 |
| GRAND | 102 | 30 | 103 | 29 | 75 | 22 | 75 | 22 |
| NGHI | 73 | 30 | 63 | 26 | 53 | 23 | 47 | 21 |
| CORD | 70 | 28 | 62 | 25 | 50 | 20 | 48 | 20 |
| Mean | 75.6 | 29 | 70.8 | 26.6 | 55 | 21.4 | 52.6 | 20.4 |
| Max velocity differential | PV: 75.6 (ADE1) − 70.8 (ADE2) = 4.8 | | | | MV: 55 (ADE1) − 52.6 (ADE2) = 2.4 | | | |
| P value | 0.12 | | | | 0.11 | | | |

No statistically significant differences (P>0.05) were noted in velocity measurements as between first and second adenosine infusions. No significant differences were noted in the occurrence of subjective symptoms (data not shown). These data confirm previous literature reports that adenosine, administered acutely, does not induce tachyphylaxis. The data serve to validate the protocol design.

In a second set of control experiments, dipyridamole was administered alone by bolus injection to 5 patients at the dosage of 28, 35 or 40 μg/kg after a three minute adenosine infusion at 140 μg/kg/min, and again after a 3 minute stabilization period. Data are shown in Table 10.

TABLE 10

| Patient ID | DIP dose (μg/kg) | PV-ADE Max | PV-ADE Min | PV-DIP Max | PV-DIP Min | MV-ADE Max | MV-ADE Min | MV-DIP Max | MV-DIP Min | Symptoms under ADE | Symptoms under DIP alone |
|---|---|---|---|---|---|---|---|---|---|---|---|
| GROS | 28 | 84 | 27 | 26 | 23 | 64 | 20 | 21 | 19 | Flushing 8/10 | None |
| COCH | 35 | 84 | 32 | 40 | 30 | 61 | 23 | 28 | 22 | Flushing 6/10 | None |
| WURI | 35 | 88 | 25 | 23 | 21 | 71 | 21 | 20 | 18 | None | None |
| STUR | 40 | 92 | 33 | 35 | 33 | 67 | 23 | 25 | 23 | Dyspnea 5/10 | None |
| TALL | 40 | 112 | 33 | 40 | 34 | 86 | 25 | 29 | 24 | None | None |

Dipyridamole did not modify peak and mean diastolic velocities. No symptoms were recorded during a follow-up of 10 minutes. The data demonstrate that intravenous bolus administration of dipyridamole as a single agent in the dosage range used in the experimental protocol, has no detectable effects; doses of dipyridamole at 28 to 40 μg/kg alone do not induce significant hemodynamic and clinical effects.

5.2 Example 2

A Phase II study was initiated to compare dipyridamole-adenosine combination administration (also termed herein, at all doses, Adenosoft™) to adenosine alone (Adenoscan®, Astellas) as a pharmacologic stressor in coronary patients undergoing single photon emission computed tomography (SPECT) imaging studies. The study, which is ongoing, is a mono-center, single-blind, 2-arm, cross-over trial.

All patients underwent a first SPECT imaging study using adenosine as single agent pharmacologic stressor at 140 μg/kg/min, according to standard clinical protocol. Only those patients in whom an ischemic zone was detected were declared eligible for the second test, and were enrolled in the study if other inclusion criteria were satisfied.

In the second test, eligible patients were stressed pharmacologically by either bolus administration of dipyridamole over 20-30 seconds, followed by adenosine infusion at 70 μg/kg/min or their concurrent administration. SPECT images were acquired as per the standard approach performed the preceding week.

Randomization of SPECT images, and their analysis by two blinded readers, took place every 10 patients. Anonymous and randomized images were assessed using the standard 17-segment model and the semi-quantitative visual score method on a 5-point scale (from 0 to 4). Safety of the procedure was analyzed as in the preceding hemodynamic study (Example 1) using a visual scale, focusing on the three most common symptoms seen with adenosine, as well as on EKG changes and other usual cardiac parameters.

The study is on-going. It will include a total of about 60 patients. Preliminary results are as follows.

About 10 patients whose participation permitted the study protocol details to be finalized have been excluded from study statistics. However they provided the following information, summarized below.

The 70 μg/kg/min adenosine+28 μg/kg dipyridamole combination provided images comparable to those provided by Adenoscan in 3 patients, but scored less well in two patients, at a level deemed unacceptable according to the study protocol. The 70 μg/kg/min adenosine+35 μg/kg dipyridamole combination provided images comparable to Adenoscan in 7 consecutive patients, while under-scoring Adenoscan in one patient, but within the acceptable limits defined by the protocol.

In five patients of this initial series, adenosine and dipyridamole were mixed together before administration and infused over 4 minutes. This modality was successful in all the patients.

The combination stressor of 40 μg/kg dipyridamole and 70 μg/kg/min adenosine was tested and showed equivalent, and sometimes better results, than Adenoscan in terms of imaging efficacy in 19 patients (10 sequential and 9 concurrent administrations). Table 11 shows the stress scores (correlated to ischemia defects) for the first 10 patients of this 40 μg/kg series (denominated, "Series I—sequential administration").

TABLE 11

| Series I | Stress score A (Adenoscan) | Stress score B (SC) | Delta score |
|---|---|---|---|
| Patient 1 | 5 | 4 | 1 |
| Patient 2 | 13 | 11 | 2 |
| Patient 3 | 5 | 5 | 0 |
| Patient 4 | 4 | 4 | 0 |

TABLE 11-continued

| Series I | Stress score A (Adenoscan) | Stress score B (SC) | Delta score |
|---|---|---|---|
| Patient 5 | 7 | 7.5 | −0.5 |
| Patient 6 | 5 | 5 | 0 |
| Patient 7 | 4 | 3 | 1 |
| Patient 8 | 14 | 14 | 0 |
| Patient 9 | 5 | 12.5 | −7.5 |
| Patient 10 | 5 | 6 | −1 |
| Total | | | −5 |

The "stress score" is the image of ischemia in one or more of the 17 cardiac segments, as scored from 0 to 4 by the blinded reader using the following scale: normal perfusion=0, mild reduction in counts=1, moderate reduction in counts=2, severe reduction=3, absence of uptake=4). Normally, a zone of ischemia is certain when a score $\geq 4$ is noted. A stress score sums the scores of all abnormal segments.

"Stress score A" is the image score difference between stress conditions between adenosine alone and rest conditions. "Stress score B" is the image score difference between stress conditions with the combination stressor—dipyridamole bolus at 40 µg/kg over 20-30 seconds. followed by adenosine infusion at 70 µg/kg/min—and resting conditions. "Delta score" is the difference between "Stress score A" and "Stress score B." It must not be >2

Since thallium is currently deemed the best isotope to test myocardial viability at rest, and sestamibi the best isotope to detect myocardial defects under stress conditions, a dual isotope myocardial scintigraphy technique was used for this study.

As seen from the data in Table 11, no patient had a delta score greater than 2: i.e., in no patient did the combination stressor perform significantly worse as compared to Adenoscan. In three (3) patients, the delta score was negative, indicating that the ischemic defects were better visualized with the combination stressor than with Adenoscan alone. Total delta score for the ten patients, which is the primary study end-point, is below 2 and even negative The second 40 µg/kg series corresponding to the concurrent administration of adenosine 70 µg/kg/mn with dipyridamole 10 µg/kg/mn is expected to provide similar results (a preliminary analysis made by a technician who does not participate to the trial indicates that images are comparable in all the patients). However the randomized analysis of this series of images by the two blinded readers with corresponding delta scores has not yet been performed (one patient missing to get to 10).

With respect to patient tolerance of the procedure, initial results are shown in Table 12 (n=27 patients). Data from these initial results indicate that there is not much difference in symptomatology between (i) 35 µg/kg dipyridamole combined with 70 µg/kg/min adenosine, and (ii) 40 µg/kg of dipyridamole combined with 70 µg/kg/min adenosine. Results are therefore cumulated, and include data from 8 patients treated with 35 µg/kg dipyridamole plus adenosine at 70 µg/kg/min, and from 19 patients treated with 40 µg/kg dipyridamole, plus adenosine at 70 µg/kg/min (SC). Given the similar adverse effect profile, the 40 µg/kg dipyridamole dose is currently preferred, since it tends to show greater efficacy. As noted above, all 27 patients were first imaged using Adenoscan alone (ADE).

TABLE 12

| Adverse events | ADE (# patients reporting event) | SC (# patients reporting event) | % reduction |
|---|---|---|---|
| Chest pain | 14 | 8 | −43% |
| Dyspnea | 11 | 9 | None |
| Flushing | 14 | 14 | None |

Note:
Reduction in the number of chest pain events among the patients (n = 19) who received dipyridamole 40 µg/kg with adenosine 70 µg/kg/mn was −45% with no difference regarding the number of other adverse events.
# = number of Table 13 gives adverse event severity cumulated scores, evaluated on a visual scale (going from 0 to 10), for the first 27 patients.

TABLE 13

| | Chest pain | Dyspnea | Flushing |
|---|---|---|---|
| Adenosine | 60 | 40 | 43.5 |
| Combination | 18.5 | 30 | 44.5 |
| % Change | −69% | −25% | +2.3% |

Note:
% of changes among the patients (n = 19) who received dipyridamole 40 µg/kg with adenosine 70 µg/kg/mn were very similar to those of the table above At this point in time, no difference in the occurrence of $A_2$ receptor-related side effects, or severity of symptoms, has become clearly apparent as between the combination stressor and Adenoscan. In contrast, the reduction in the occurrence (−43%) and severity (−69%) of chest pain (an $A_1$ receptor-related adverse effect) has already become manifest in the first 27 patients. So too has reduction in ST changes on EKG, which are fewer and less severe during testing with the combination as compared to Adenoscan: in 27 patients tested to date, only 6 patients have ST variations. The difference in ST-variation for each patient alone is not significant, but the total difference has achieved significance, with a clear trend in favor of the combination. In the table below (Table 14) ST-changes/baseline are expressed in millimeters.

TABLE 14

| Patient ID | Adenosine 140 µg/kg/mn | Combination |
|---|---|---|
| N° 5 | 0.5 | 0 |
| N°12 | 1 | 0.1 |
| N°14 | 0.8 | 0.3 |
| N°16 | 1 | 0.7 |
| N°17 | 1.2 | 0.9 |
| N°24 | 1 | 0 |
| Total | 5.5 | 2 |

5.3 Example 3

A study was undertaken to assess pharmacological properties of a pharmaceutical composition comprising adenosine and dipyridamole at an A:D weight ratio of 7:1. In particular, the study was conducted to assess the properties of a composition comprising adenosine at a concentration of 7 mg/ml and dipyridamole at a concentration of 1 mg/ml. This particular formulation is very convenient, since it permits the use of plain figures for calculating concentrations, maximal volumes, and weights—which is useful to reduce dosing errors in the clinical setting—while also covering a wide range of needs, as shown in the table below:

TABLE 15

| Adenosine concentration (mg/ml) | Volume (ml) | Total amount of adenosine per unit (mg) | Maximal patient weight covered (kgs) | Total amount of dipyridamole per unit (mg) |
|---|---|---|---|---|
| 7 | 2 | 14 | 50 | 2 |
|   | 3 | 21 | 75 | 3 |
|   | 4 | 28 | 100 | 4 |
|   | 5 | 35 | 125 | 5 |
|   | 6 | 42 | 150 | 6 |
|   | 8 | 56 | 200 | 8 |

Dipyridamole is poorly soluble in saline and is unstable in the long term in solvents at pH >4. Adenosine compositions currently used in clinical practice have pH >4, and are thus poorly suited to addition of dipyridamole. Therefore, a more acidic pH was chosen. The lower pH also increases adenosine solubility above 4 mg/ml, which is the upper acceptable adenosine concentration limit in saline.

The following composition was prepared:

TABLE 16

| Component | Final concentration | Supplier | Reference |
|---|---|---|---|
| Adenosine | 7 mg/ml | Sigma Aldrich | Eur. Ph. January 2005: 1486 |
| Dipyridamole | 1 mg/ml | Sigma Aldrich | Eur. Ph. January 2005: 1199 |
| Polyethyleneglycol 600 | 50 mg/ml | SASOL | Eur. Ph.. January 2005: 1444 |
| Tartaric acid | 2 mg/ml | Sigma Aldrich | Eur. Ph.. January 2005: 0460 |
| Water for injection | — (1 ml) | Aguettant | AMM: 319 508.5 |

After sonication for 2 minutes and magnetic stirring for 10 minutes, the solution became completely clear with a pH of 3.6 and an osmolality of 151 mosmol/kg.

In summary, adenosine (Adenoscan, Astellas) is the standard pharmacological stressor used in cardiac imaging to induce near-maximal coronary vasodilation. At its recommended dosage rate of 140 µg/kg/min, its use is attended by numerous uncomfortable side effects. The data from these studies demonstrate that the sequential bolus administration of dipyridamole at 28-40 µg/kg—well below the total dose infused when dipyridamole is used as a single agent stressor—followed by infusion of adenosine at 70 µg/kg/min, is equally efficacious in providing coronary vasodilation for imaging studies, while causing fewer side effects. The data also demonstrate that dipyridamole and adenosine may be combined in a single infusion, over 4 minutes, to similar effect. Among the side effects reduced by the combination of the present invention are chest pain, and the risk of significant heart blockage.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. A method of inducing coronary vasodilation in a patient for use in cardiac diagnosis, the method comprising:
   parenterally administering dipyridamole to said patient; and
   concurrently or sequentially thereafter parenterally administering adenosine to said patient,
   wherein dipyridamole is administered intravenously at a total dose of 23-40 µg/kg, and adenosine is administered intravenously at a dosage rate of 35 µg/kg/min-100 µg/kg/min.

2. The method of claim 1, wherein dipyridamole is administered as a bolus.

3. The method of claim 2, wherein adenosine is administered at a dosage rate of 50 to 70 µg/kg/min.

4. The method of claim 3, wherein adenosine is administered at a dosage rate of 70 µg/kg/min.

5. The method of any one of claims 2-4, wherein dipyridamole is administered at a total dose of 40 µg/kg.

6. The method of claim 1, wherein dipyridamole is administered at a total dose of 40 µg/kg.

7. The method of claim 1, wherein dipyridamole is administered as an intravenous infusion.

8. The method of claim 7, wherein adenosine is administered at a dosage rate of 50 to 70 µg/kg/min.

9. The method of claim 8, wherein adenosine is administered at a dosage rate of 70 µg/kg/min.

10. The method of any one of claims 7-9, wherein dipyridamole is administered at a dosage rate of 10 µg/kg/min.

11. The method of claim 7, wherein dipyridamole is administered continuously for 2 to 4 minutes.

12. The method of claim 8, wherein dipyridamole is administered continuously for 2 to 4 minutes.

13. The method of claim 9, wherein dipyridamole is administered continuously for 2 to 4 minutes.

14. The method of claim 10, wherein dipyridamole is administered continuously for 2 to 4 minutes.

15. The method of claim 1, wherein adenosine is administered at a dosage rate of 50 to 70 µg/kg/min.

16. The method of claim 15, wherein adenosine is administered at a dosage rate of 70 µg/kg/min.

17. The method of any one of claims 15-16, wherein adenosine is administered continuously for less than 6 minutes.

18. The method of claim 17, wherein dipyridamole is administered continuously for 2 to 4 minutes.

19. The method of claim 1, wherein adenosine is administered sequentially after dipyridamole is administered.

20. The method of claim 19, wherein dipyridamole is administered as a bolus.

21. The method of claim 20, wherein dipyridamole is administered at a total dose of 40 µg/kg.

22. The method of any one of claims 19-21, wherein adenosine is administered at a dosage rate of 70 μg/kg/min.

23. The method of claim 22, wherein adenosine is administered continuously for 2 to 4 minutes.

24. The method of any one of claims 1, 2, 7, 15, or 19, further comprising:
assessing cardiac function using one or more technique selected from the group consisting of: electrocardiography, M mode echography, two dimensional echography, three dimensional echography, echo-doppler, cardiac imaging, planar (conventional) scintigraphy, single photon emission computed tomography (SPECT), dynamic single photon emission computed tomography, positron emission tomography (PET), first pass radionuclide angiography, equilibrium radionuclide angiography, nuclear magnetic resonance (NMR) imaging, perfusion contrast echocardiography, digital subtraction angiography (DSA), and ultrafast x-ray computed tomography (CINE CT).

25. The method of claim 24, wherein cardiac function is assessed by cardiac imaging.

26. The method of claim 25, wherein cardiac imaging is performed using SPECT.

27. The method of claim 25, wherein cardiac imaging is performed using PET.

28. The method of claim 1, wherein adenosine and dipyridamole are administered at an adenosine:dipyridamole weight ratio of 2:1 to 10:1.

29. The method of claim 28, wherein adenosine and dipyridamole are administered at an adenosine:dipyridamole weight ratio of 7:1.

30. The method of claim 1, wherein adenosine and dipyridamole are administered concurrently.

31. The method of claim 30, wherein adenosine and dipyridamole are administered as two separate compositions.

32. The method of claim 30, wherein adenosine and dipyridamole are administered as a single composition.

33. The method of claim 30, wherein adenosine is administered at a dosage rate of 70 μg/kg/min.

34. The method of claim 30 or 33, wherein dipyridamole is administered at a dosage rate of 10 μg/kg/min.

35. The method of claim 30, wherein adenosine and dipyridamole are administered in an adenosine:dipyridamole weight ratio of 2:1 to 10:1.

36. The method of claim 35, wherein adenosine and dipyridamole are administered in an adenosine:dipyridamole weight ratio of 7:1.

37. The method of claim 30, wherein adenosine is administered continuously for 2 to 4 minutes.

38. The method of claim 30, further comprising:
assessing cardiac function using one or more technique selected from the group consisting of: electrocardiography, M mode echography, two dimensional echography, three dimensional echography, echo-doppler, cardiac imaging, planar (conventional) scintigraphy, single photon emission computed tomography (SPECT), dynamic single photon emission computed tomography, positron emission tomography (PET), first pass radionuclide angiography, equilibrium radionuclide angiography, nuclear magnetic resonance (NMR) imaging, perfusion contrast echocardiography, digital subtraction angiography (DSA), and ultrafast x-ray computed tomography (CINE CT).

39. The method of claim 38, wherein cardiac function is assessed using cardiac imaging.

40. The method of claim 39, wherein cardiac imaging is performed using SPECT.

41. The method of claim 39, wherein cardiac imaging is performed using PET.

* * * * *